US007918898B2

(12) United States Patent
Andrysek (10) Patent No.: US 7,918,898 B2
(45) Date of Patent: Apr. 5, 2011

(54) ARTIFICIAL JOINT WITH LOCKING MECHANISM (75) Inventor: Jan Andrysek, Toronto (CA)

(73) Assignee: Bloorview Kids Rehab, Toronto (CA)

( * ) Notice: Subject to any disclaimer, the term of this patent is extended or adjusted under 35 U.S.C. 154(b) by 640 days.

(21) Appl. No.: 11/564,897

(22) Filed: Nov. 30, 2006

(65) Prior Publication Data
US 2008/0133019 A1 Jun. 5, 2008

(51) Int. Cl.
A61F 2/64 (2006.01)
A61F 2/68 (2006.01)
(52) U.S. Cl. ......................................................... 623/43
(58) Field of Classification Search .................. 623/43; 606/26
See application file for complete search history.

(56) References Cited

U.S. PATENT DOCUMENTS

| 2,489,291 | A | * | 11/1949 | Henschke et al. | 623/41 |
| 2,561,370 | A | * | 7/1951 | Henschke et al. | 623/26 |
| 3,533,651 | A | * | 10/1970 | Prahl | 403/93 |
| 5,267,950 | A | | 12/1993 | Weddendorf | |
| 6,423,098 | B1 | * | 7/2002 | Biedermann | 623/24 |
| 6,911,050 | B2 | * | 6/2005 | Molino et al. | 623/43 |
| 2002/0183673 | A1 | | 12/2002 | Naft | |
| 2005/0149203 | A1 | * | 7/2005 | Andrysek et al. | 623/44 |

* cited by examiner

Primary Examiner — Bruce E Snow
Assistant Examiner — Melissa Hoban
(74) Attorney, Agent, or Firm — Pillsbury Winthrop Shaw Pittman LLP (57) ABSTRACT An artificial joint including a main body and a lower portion adapted to pivotally engage the main body about a control axis while having a locking means that is integral with the lower portion. An upper portion adapted to pivotally engage the main body about a flexing axis and has an engagement means adapted to engage and disengage the locking means upon the pivoting rotation of the upper portion relative the main body. A biasing means is adapted to engage both the main body and the lower portion thereby biasing the locking means to engage the engagement means, and at least one stopping surface adapted to limit motion between the main body and the lower portion. The locking means is activated when a load is imposed on the artificial joint and passes through a line posterior to the control axis, and is de-activated when the load passes through a line anterior to the control axis.

24 Claims, 8 Drawing Sheets

ARTIFICIAL JOINT WITH LOCKING MECHANISM

FIELD OF THE INVENTION

This invention relates in general to artificial joints and more particularly to an artificial knee joint for use in prosthetic or orthotic applications having a locking means that provides support, stability and unrestricted motion.

BACKGROUND OF THE INVENTION

Artificial joints generally utilize a variety of mechanisms to control their movement and to provide support and stability. Specifically an artificial knee joint needs to bend or articulate during sitting, kneeling or ambulating. By providing improved control of the leg during the swing-phase of the gait when the person is walking or running, one also improves the look of the gait and makes the gate look more natural.

Improved support and stability when one is standing or putting weight on the leg is critical during the support-phase or stance-phase of the gait cycle otherwise the artificial joint may bend uncontrollably causing the amputee to fall. Amputees have some control during stance by the way they load the leg and how they use their remaining muscles at the hip. Alternatively, a prosthetist can align a prosthesis to be more or less stable by placing the knee joint axis behind the load bearing plane or load line. However, this tends not to produce ideal gait characteristics.

Many different designs for artificial knee joints have been proposed to address the issue of support/stance-phase control, including a built-in "locking" mechanism for this purpose. Typically, these designs are joints which lock manually during ambulation so that the person has a choice of walking with his leg locked in extension or in a free swing. If the locked position is chosen, the person is forced to walk stiff legged. However, as noted above flexing at the knee during walking may result in uncontrollable movement and a buckling of the person's leg.

Artificial joints with automatically engaging locking mechanisms also have some major disadvantages. One disadvantage in current automatic locking mechanisms is that the automatic locking can occur only when the user has achieved full extension of the knee. The timing of the locking can cause an accident for the person as they may not be able to fully extend the knee before loading or placing weight on the leg. This would result in the knee to fold uncontrollably and allow the person to fall as noted above. Another disadvantage relates to the fact that although the locking mechanism automatically locks, these joints require manual operation to disengage or unlock the joint. This in turn requires that the user must have a free hand to activate the disengagement mechanism and could discourage the user from the therapeutic bending of the knee.

Prior art artificial joints have been devised to address some of the noted problems. For example, US Patent Application 2002/0183673 A1 by Naft discloses an electromechanical orthotic knee joint. It uses sensors that electronically provide signals to actuate a magnetic coil that brings together a set of serrated disks, thus preventing flexion. U.S. Pat. No. 5,267,950 issued to Weddendorf on Dec. 7, 1993 discloses an orthotic knee joint mechanism that under loading presses a set of bevelled serrated members into a bevelled surface, thus locking the knee. When unloaded the surfaces are not engaged and flexion/extension at the knee joint is possible.

Thus an artificial joint with a locking mechanism which provides improved stabilization and support while at the same time providing unrestricted motion is desirable.

SUMMARY OF THE INVENTION

An object of one aspect of the present invention is to provide an improved artificial joint having an automatic locking means.

In accordance with one aspect of the present invention there is provided an artificial joint including a main body and a lower portion adapted to pivotally engage the main body about a control axis while having a locking means that is integral with the lower portion. The artificial joint further includes an upper portion adapted to pivotally engage the main body about a flexing axis and has an engagement means adapted to engage and disengage the locking means upon the pivoting rotation of the upper portion relative the main body.

The artificial joint further includes a biasing means adapted to engage both the main body and the lower portion thereby biasing the locking means to engage the engagement means, and at least one stopping surface adapted to limit motion between the main body and the lower portion. An additional stopping surface is included to limit the motion of the upper portion. The locking means is engaged when a load is imposed on the artificial joint and passes through a line posterior to the control axis, and is disengaged when the load passes through a line anterior to the control axis.

Preferably, the locking means is a latch member integral with the lower portion. Conveniently when the artificial joint is a knee joint for example, the latch member may be position in the front of the artificial joint or in the rear of the artificial joint. Furthermore the artificial joint may also include a swing-phase control means.

Preferably the biasing means is a spring to bias the latch member in the engaged position. The stopping surfaces may include resilient material to help dampen impact during various movements of the artificial joints.

Advantages of the present invention are automatic engagement and disengagement of the locking means, improved stabilization and support when weight is placed on the joint while providing unrestricted motion, the locking means may be placed in the front or rear of the artificial joint depending on its intended use, simplified design, more compact design relative to traditional artificial joints, reduced manufacturing costs, for use as an orthotic, prosthetic or robotic joint and may be used as a knee joint or elbow joint.

BRIEF DESCRIPTION OF THE DRAWINGS

A detailed description of the preferred embodiments is provided herein below by way of example only and with reference to the following drawings, in which:

FIG. 2b in a side view, illustrates the artificial joint of FIG. 1b in a disengaged position.

FIG. 3b in a side view, illustrates the artificial joint of FIG. 1b in an engaged position.

FIG. 4b in a side view, illustrates the artificial joint of FIG. 1b during gait.

FIG. 5b in a side view, illustrates the artificial joint of FIG. 1b during gait.

FIG. 6b in a side view, illustrates the artificial joint of FIG. 1b during gait.

FIG. 7b in a side view, illustrates the artificial joint of FIG. 1b during gait.

In the drawings, preferred embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENT

Figure 1A:
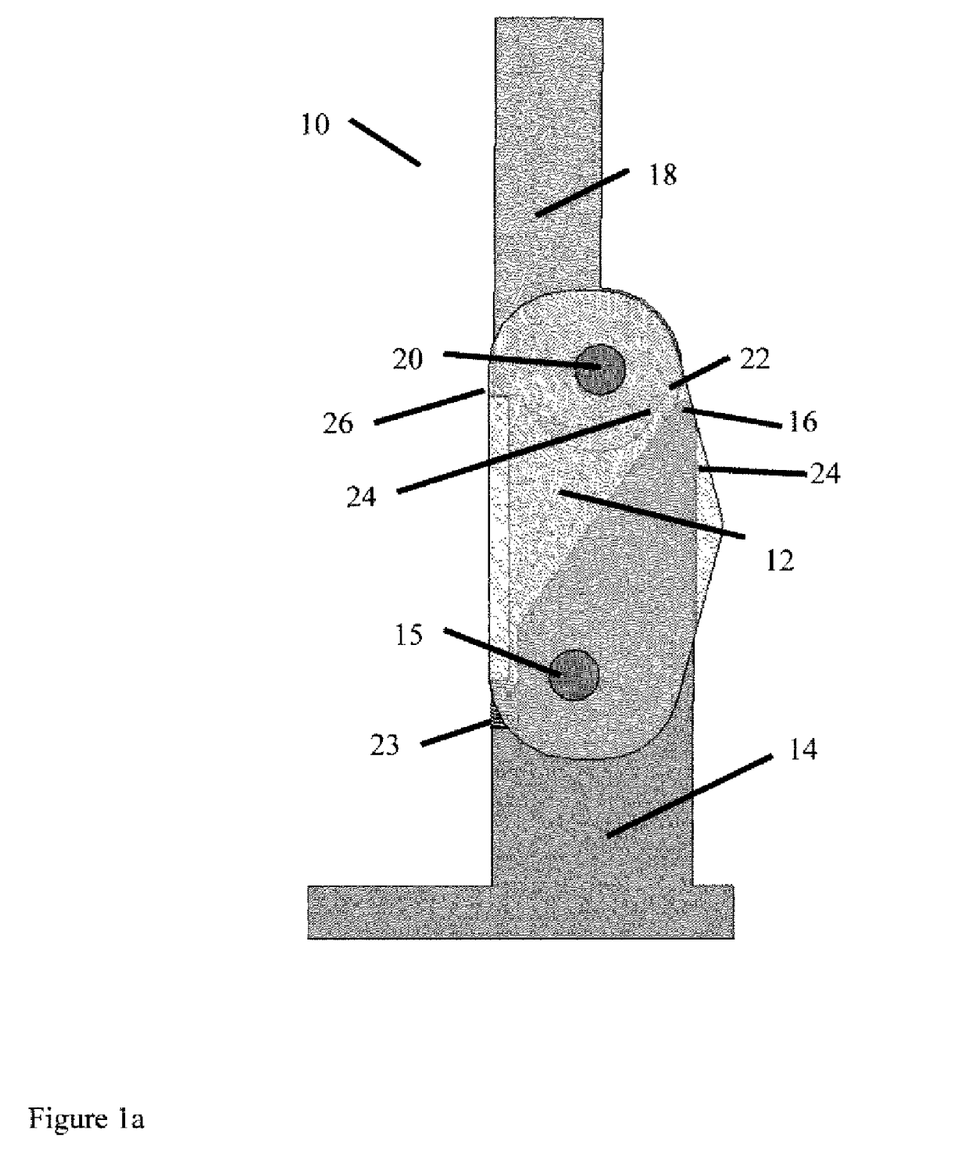
FIG. 1a in a side view, illustrates an artificial joint having the locking means in the back of the joint in accordance with a preferred embodiment of the present invention.
Figure 1B:
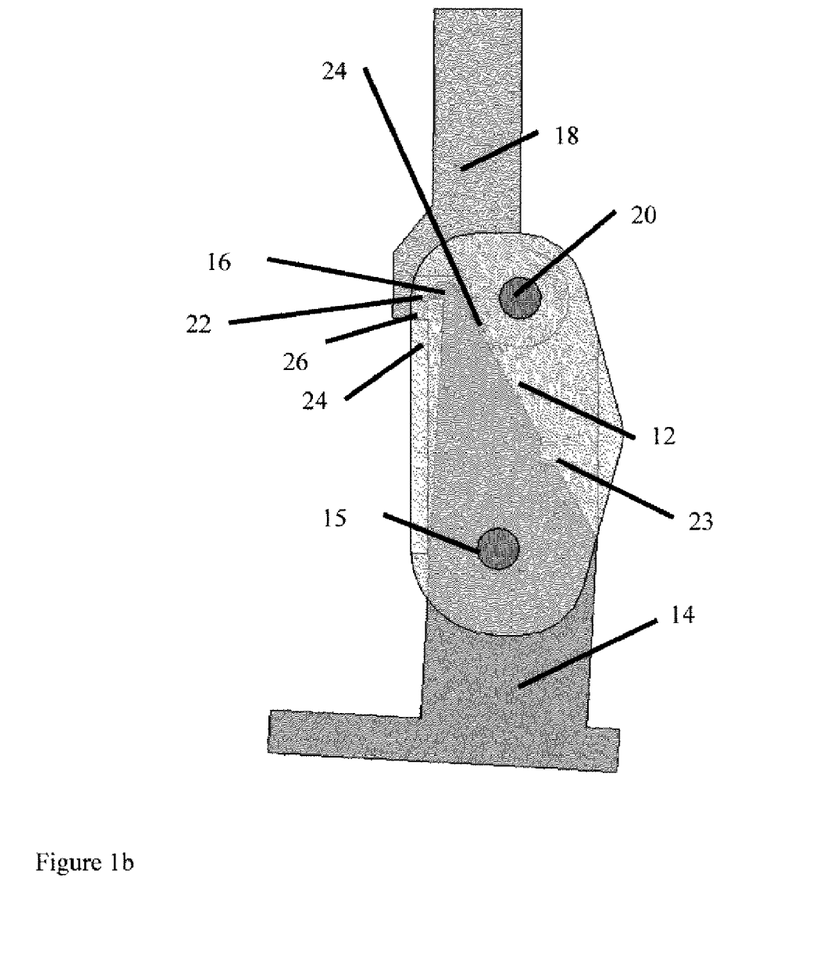
FIG. 1b in a side front view, illustrates an artificial joint having the locking means in the front of the joint in accordance with a preferred embodiment of the present invention.
Figure 2A:
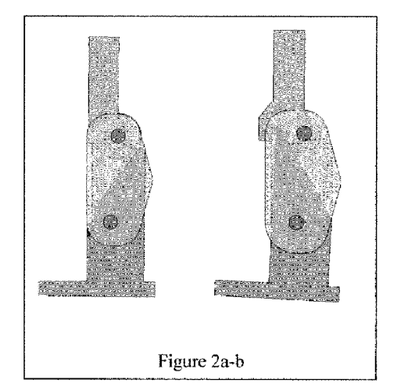
FIG. 2a in a side view, illustrates the artificial joint of FIG. 1a in a disengaged position.
Figure 3A:
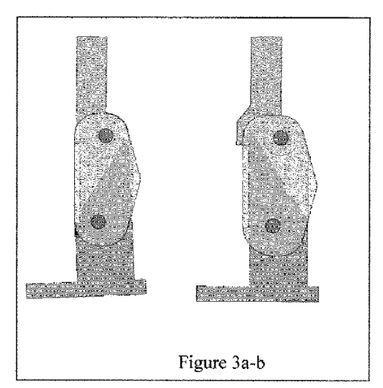
FIG. 3a in a side view, illustrates the artificial joint of FIG. 1a in an engaged position.
Figure 4A:
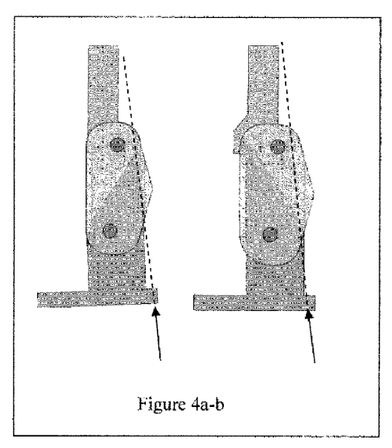
FIG. 4a in a side view, illustrates the artificial joint of FIG. 1a during gait.
Figure 5A:
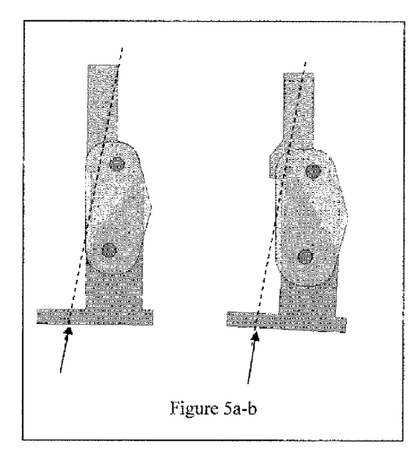
FIG. 5a in a side view, illustrates the artificial joint of FIG. 1a during gait.
Figure 6A:
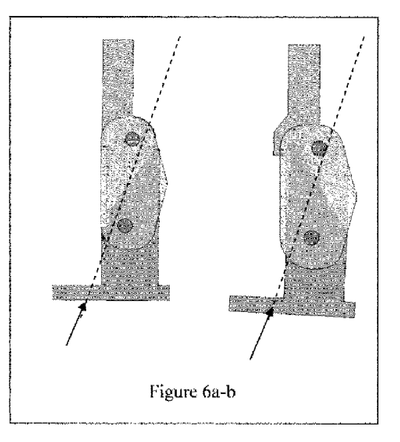
FIG. 6a in a side view, illustrates the artificial joint of FIG. 1a during gait.
Figure 7A:
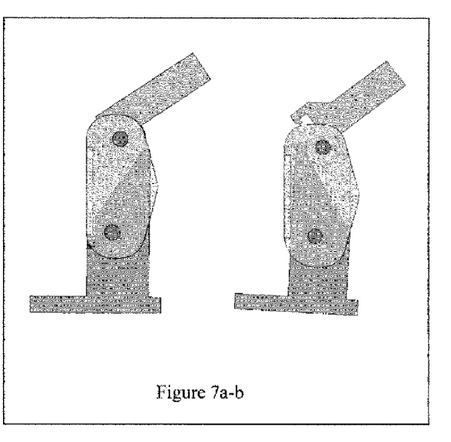
FIG. 7a in a side view, illustrates the artificial joint of FIG. 1a during gait.
Figure 8:
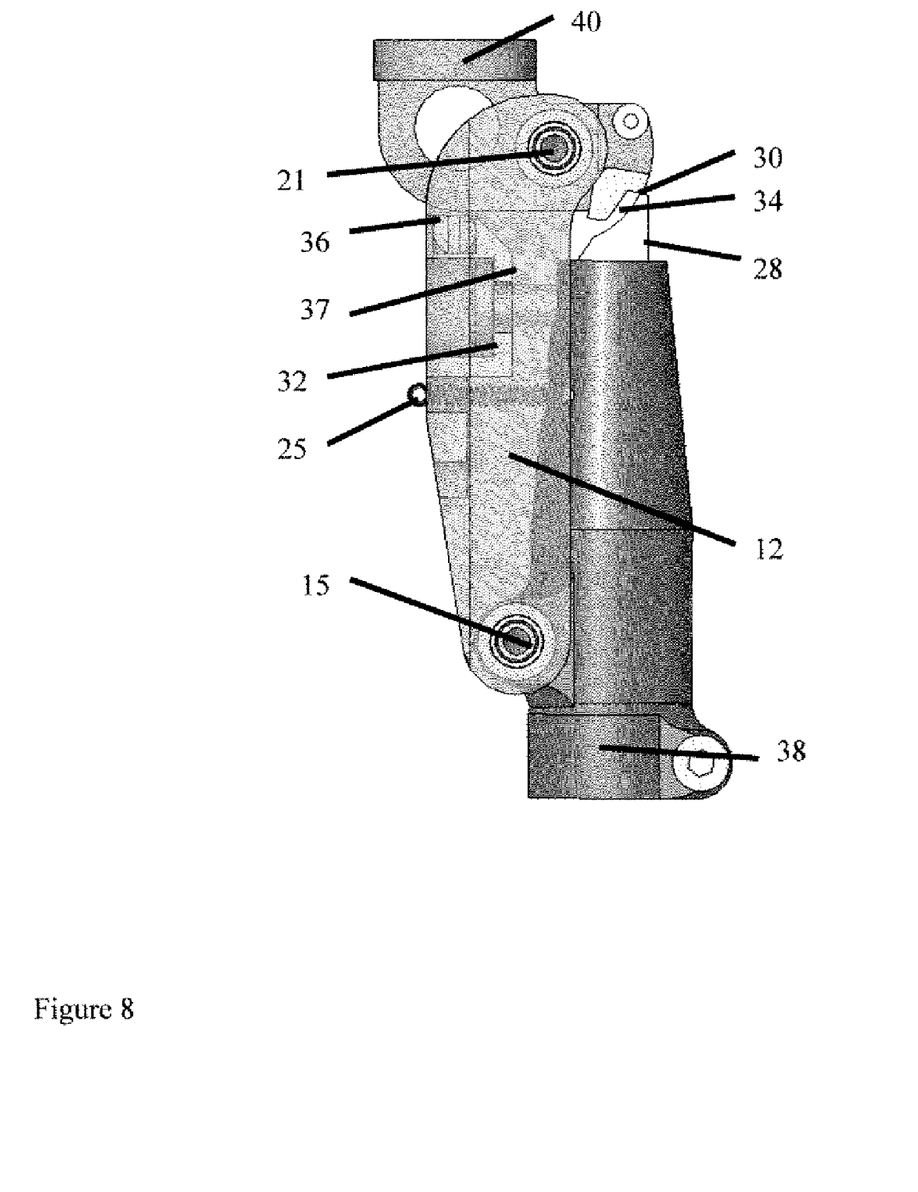
FIG. 8 in a side view, illustrates the artificial joint of FIG. 1a in a prosthetic knee joint.
Figure 9:
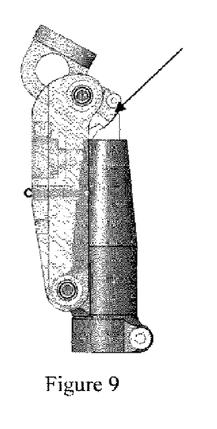
FIG. 9 in a side view illustrates the artificial joint of FIG. 8 during flexing of the joint.

Referring to FIG. 1, there is illustrated in a side view, an artificial joint 10 in accordance with a preferred embodiment of the present invention. The artificial joint 10 includes a main body 12 and a lower portion 14 adapted to pivotally engage the main body 12 about a control axis 15 while having a locking means 16 that is integral with the lower portion 14. The artificial joint 10 further includes an upper portion 18 adapted to pivotally engage the main body 12 about a flexing axis 20 and has an engagement means 22 adapted to engage and disengage the locking means 16 upon the pivoting rotation of the upper portion 18 relative the main body 12. The pivotal rotation of the upper portion 18 relative to the main body 12 also allows for the articulation or flexion and extension of the joint when the locking means 16 is disengaged from the engagement means 22.

The artificial joint 10 further includes a biasing means 22 adapted to engage both the main body 12 and the lower portion 14 thereby biasing the locking means 16 in an engaged position. At least one stopping surface 24 is adapted to limit motion between the main body 12 and the lower portion 14. An additional stopping surface 26 is included to limit the motion of the upper portion 18. The locking means 16 is engaged when a load is imposed on the artificial joint 10 and passes through a line posterior to the control axis 15, and is disengaged when the load passes through a line anterior to the control axis 15.

The locking means 16 may be further defined as a latch member 28 or similar latching mechanism that is integral with the lower portion 14. By having the latch member 28 integral with the lower portion 14, the design of the artificial joint 10 can be compact and simplified. The engagement means 22 may be further defined as a step 30 that is adapted to engage the latch member 28. The step 30 is integral with the upper portion 18 thereby contributing to the compactness and simplification of the design of the artificial joint 10. The biasing means 22 may be defined as a spring 24 such as an extension spring.

The stopping surfaces 24 and 26 may include a resilient material to dampen impact during their engagement. The stopping surfaces may also be adjustable. The stopping surfaces 24 may be further defined as a first stopping surface 32 that limits the motion of the lower portion 14 by its engagement with the main body 12 when the artificial joint 10 is in a disengaged position, and a second stopping surface 34 that limits the motion of the lower portion 14 be its engagement with the main body 12 when the artificial joint is in an engaged position. The stopping surface 26 may be further defined as a stopping surface 36 that limits the movement of the upper portion 18 relative the main body 12 when the artificial joint 10 is in a fully extended position.

The artificial joint 10 may have a number of applications such as a prosthetic, orthotic or robotic joint, and may be used for a knee or elbow by way of example only. More specifically the use of the artificial joint 10 as a knee joint allows for different positioning of the locking means 16 or latch member 28 in the artificial joint 10. For example the locking means 16 may be positioned at the rear of the knee joint or at the front of the knee joint. The preferred positioning of the locking means 16 will depend on the how the artificial joint 10 is being used. When the artificial joint 10 is applied to a prosthetic, the locking means 16 may be positioned in the front so as to have improved flexion of the artificial joint 10. When the artificial joint 10 is applied to an orthotic, the locking means 16 may be positioned in the back.

When the artificial joint 10 is utilized as a knee joint with the locking means 16 positioned in either the front or the back of the artificial joint 10, the lower portion 14 may be further defined as a shank portion 38 and the upper portion 18 may be defined as a thigh portion 40. Typically the thigh portion 40 will attach to the thigh part of the prosthesis or orthosis and the shank portion 38 will attach to the shank part of prosthesis or orthosis. The flexing axis 20 may be further defined as a knee axis 21 that allows for the knee joint to articulate as an anatomical knee might, the thigh portion 40 relative to the shank portion 38. The knee axis 21 is located above the control axis 15.

The artificial joint 10 may also include a swing phase-control means 42. The swing phase-control means 42 includes a piston and cylinder assembly 44 that has a first end 46 adapted to engage the upper portion 18 or thigh portion 40, and a second end 48 adapted to engage the lower portion 14 or the shank portion 38. The piston and cylinder assembly 44 may be hydraulic, spring-assisted or pneumatic.

Referring to FIGS. 2a to 7b, during typical gait motion the artificial joint 10 in a knee having both the latch member in the front and the back, functions in the following way. The knee joint extends at the end of the swing-phase and the thigh portion 40 engages stopping surface 26. At this point the locking means 16 and the engagement means 22 become aligned and the shank portion 38 pivots relative to the main body 12 with the assistance of the biasing means 22 so that locking means 16 engages the engagement means 22.

The stance phase commences when the person places weight on the leg and therefore has foot contact. Typically initial contact with the ground surface will generally be made at the rear of the foot. In an artificial joint 10 that does not have a lock, the force of loading will generally result in a knee flexion moment that will cause knee flexion and hence knee instability. With artificial joint 10, such flexion is prevented by the engagement of the locking means 16. Specifically the flexion moment about the control axis 15, acts to push the locking means 16 securely against the second stopping surface 34 therefore further securing the engagement of the locking means 16. Toward the end of the stance-phase, the loading transfers to the forefoot. This extension moment about control axis 15 causes the shank portion 38 to pivot to disengage the locking means 16. The knee joint can now be voluntarily flexed by applying a hip flexion moment thereby beginning of the swing-phase.

Referring to FIGS. 8 to 11 when the artificial joint 10 is applied to a prosthetic knee with the locking means 16 in the rear of the artificial joint 10, some modifications may be required. Specifically the thigh portion 40 further includes a first coupling means for connecting the thigh portion 40 of the prosthesis and a second coupling means for connecting the shank portion 38 of the prosthesis. As noted above the stopping surfaces 36 and 34 may include resilient material to dampen the impact during knee extension and impact of the locking means 16. Stopping surface 32 may be further defined as the head of a screw that threads into the shank portion at the front of the knee joint. With this arrangement the distance of stopping surface 32 can be adjusted to minimize the gap between locking means 16 and thigh portion 40 as the knee joint is being flexed.

Figure 10:
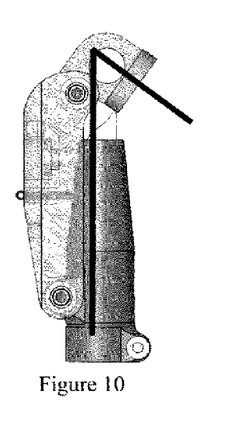
FIG. 10 in a side view illustrates the artificial joint of FIG. 8 during flexing of the joint.
Figure 11:
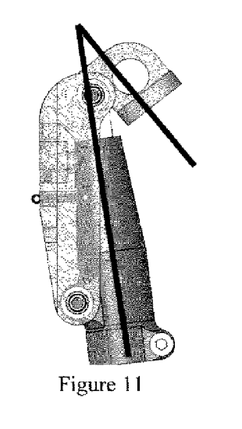
FIG. 11 in a side view illustrates the artificial joint of FIG. 8 during flexing of the joint.
Figure 12:
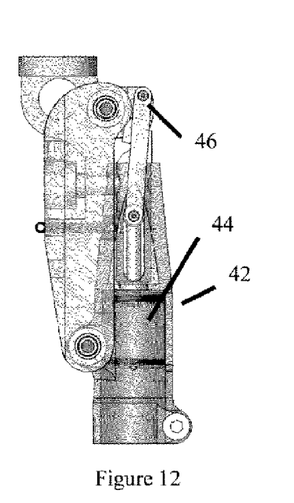
FIG. 12 in a side view illustrates the artificial joint of FIG. 8 including a swing-phase control means.
Figure 13:
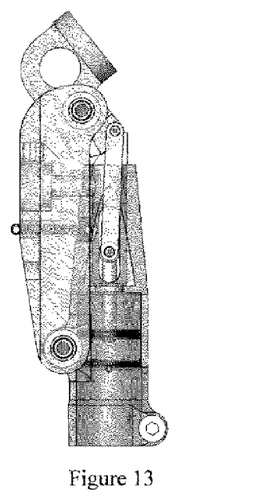
FIG. 13 in a side view illustrates the artificial joint of FIG. 12 including a swing-phase control means.
Figure 14:
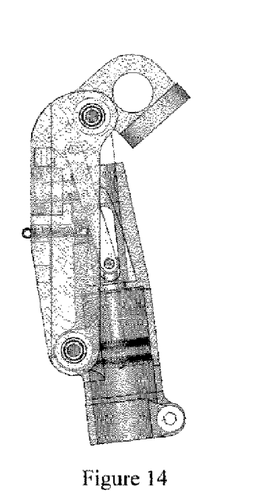
FIG. 14 in a side view illustrates the artificial joint of FIG. 12 including a swing-phase control means.

The biasing means 22 may be an extension spring used to pull the shank portion 38 into the lock-engaged position. In this embodiment the distance between knee axis 21 and control axis 15 is maximized to limit the amount of pivoting and therefore motion by the shank portion 38 needed to engage and disengage the locking means 16, thereby reducing the feeling of instability in the artificial joint 10. Excessive motion may also be eliminated by the proper adjustment of stopping surface 32. FIGS. 10 and 11 represent various degrees of knee flexion with and without the additional flexion at the control axis 15 of the shank portion 38 during kneeling. Stopping surface 37 defines the final resting position of the shank portion 38. The swing phase-control means 42 referred to in FIGS. 12 to 14 may be easily included into the artificial joint 10. The piston and cylinder assembly 44 impacts the artificial joint 10 as it partially resists the motion of the thigh portion 40 relative to the main body 12 and/or shank portion 38.

Figure 15:
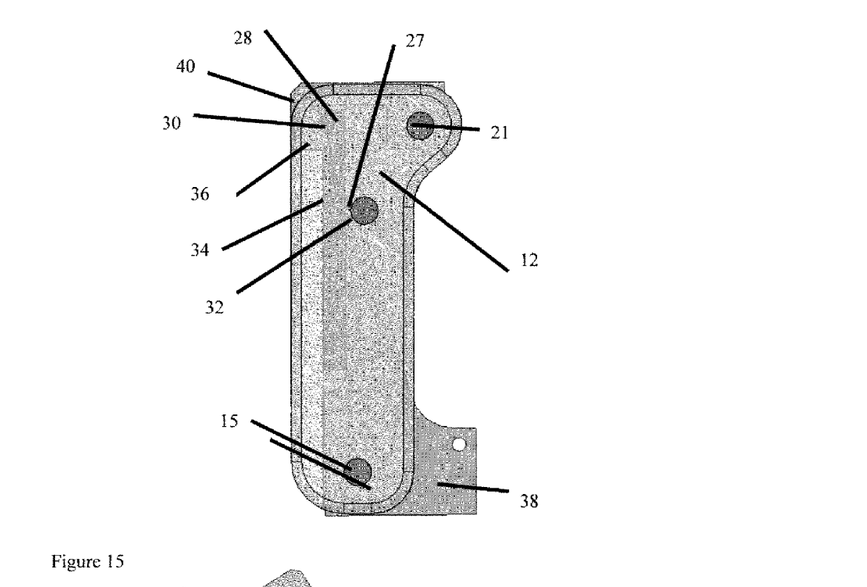
FIG. 15 in a side view illustrates the artificial joint of FIG. 1b in a prosthetic knee joint.
Figure 16:
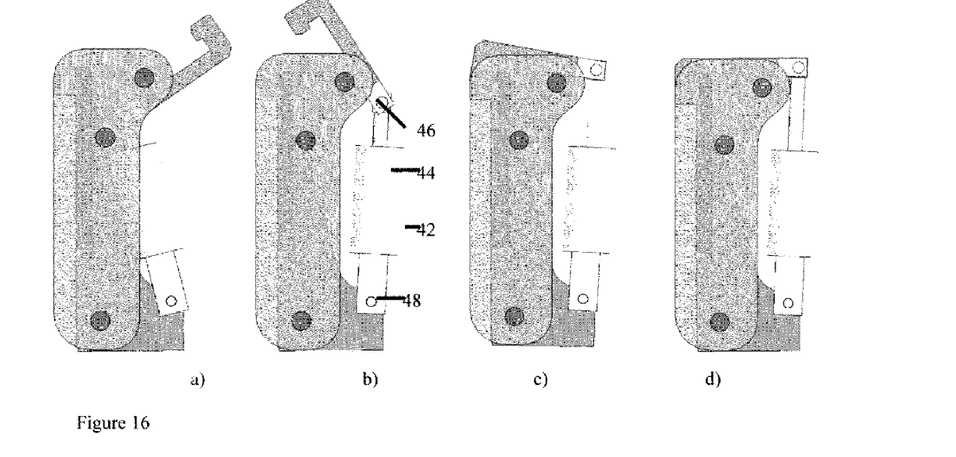
FIG. 16a in a side view illustrates the artificial joint of FIG. 15 including a swing-phase control means.
FIG. 16b in a side view illustrates the artificial joint of FIG. 15 including a swing-phase control means.
FIG. 16c in a side view illustrates the artificial joint of FIG. 15 including a swing-phase control means.
FIG. 16d in a side view illustrates the artificial joint of FIG. 15 including a swing-phase control means.

FIG. 15 illustrates the artificial joint 10 as a prosthetic knee joint with the locking means 16 in the front of the knee joint. This embodiment may have the similar modifications as when the locking means 16 is positioned in the rear of the artificial joint 10. Specifically, the first stopping surface 32 may actually be integral with the main body 12. Furthermore this embodiment may include the swing phase-control means 42 as depicted in FIGS. 16a to 16c.

Figure 17:
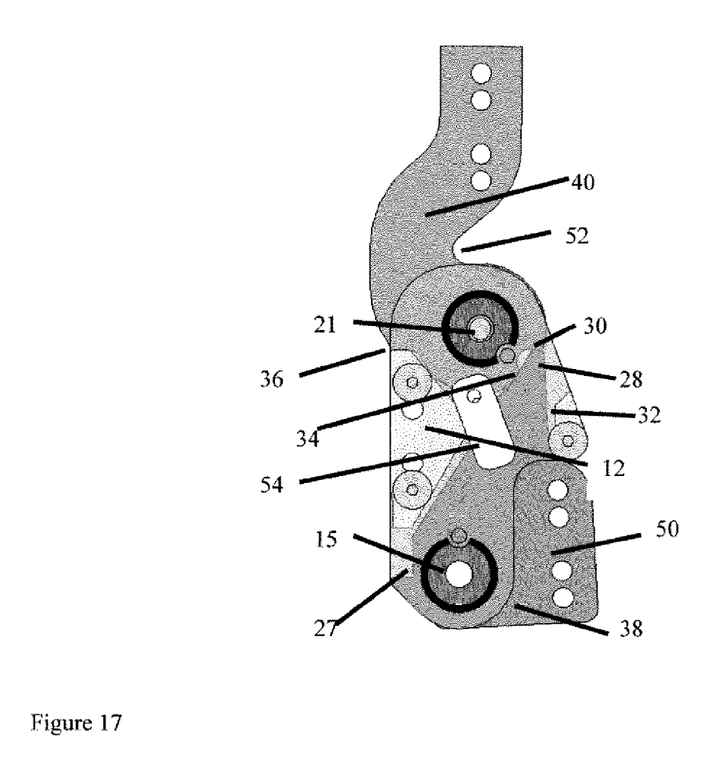
FIG. 17 in a side view illustrates the artificial joint of FIG. 1a in an orthotic knee joint.
Figure 18:
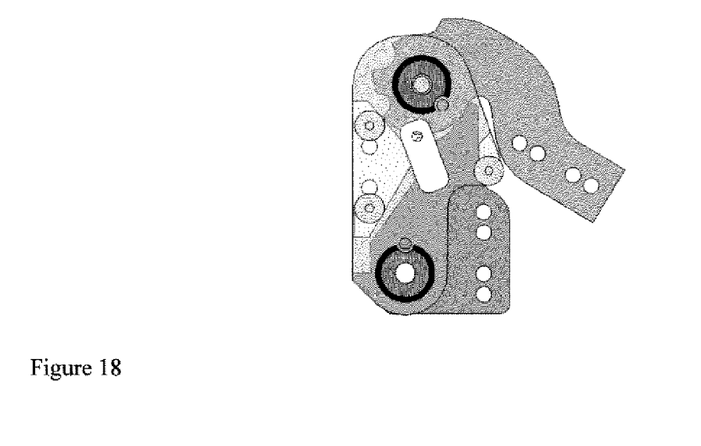
FIG. 18 in a side view illustrates the artificial joint of FIG. 17.

Referring to FIGS. 17 and 18 the artificial joint 10 may be applied to an orthotic knee joint having the locking means 16 in the rear of the knee joint. This embodiment may require modifications namely a reduced length of the overall artificial joint 10 achieved by proximally relocating the shank portion 38 using a shank portion connection 50 and providing a clearance 52 for the thigh portion 40 so that knee flexion is still possible. A manual locking mechanism 54 for overriding the automatic engagement and disengagement of the locking means 16 may also be included to provide extra stability by being able to lock the artificial joint 10 and walking stiff-legged.

Other variations and modifications of the invention are possible. All such modifications or variations are believed to be within the sphere and scope of the invention as defined by the claims appended hereto.

I claim:

1. An artificial joint for providing pivotal movement between a first body member and a second body member comprising:
   (a) a main body;
   (b) a lower portion that connects to the first body member and is adapted to pivotally engage the main body about a control axis, the lower portion including a locking means integral therewith which pivots only about the control axis;
   (c) an upper portion that connects to the second body member and is adapted to pivotally engage the main body about a flexing axis and having an engagement means adapted to engage and disengage the locking means upon the pivoting rotation of the upper portion relative the main body;
   (d) a biasing means adapted to engage both the main body and the lower portion thereby biasing the locking means to engage the engagement means;
   (e) at least one stopping surface adapted to limit motion between the main body and the lower portion; and
   (f) at least one stopping surface adapted to limit motion of the upper portion;
      wherein the locking means is engaged when a load is imposed on the artificial joint that passes through a line posterior to the control axis, and is disengaged when the load passes through a line anterior to the control axis.

2. An artificial joint as claimed in claim 1 wherein the locking means is a latch member.

3. An artificial joint as claimed in claim 2 wherein the engagement means is a step adapted to engage the latch member.

4. An artificial joint as claimed in claim 1 wherein the biasing means is a spring.

5. An artificial joint as claimed in claim 1 wherein the stopping surfaces include a resilient material.

6. An artificial joint as claimed in claim 5 wherein the stopping surfaces are adjustable.

7. An artificial joint as claimed in claim 5 wherein the stopping surfaces are a first stopping surface limiting the motion of the lower portion by its engagement with the main body in a disengaged position and a second stopping surface limiting the motion of the lower portion by its engagement with the main body in an engaged position.

8. An artificial joint as claimed in claim 5 wherein one of the stopping surfaces limits the upper portion when the artificial joint is in a fully extended position.

9. An artificial joint as claimed in claim 1 wherein the artificial joint is used as a prosthetic, orthotic or robotic joint.

10. An artificial joint as claimed in claim 9 wherein the artificial joint is a knee joint.

11. An artificial joint as claimed in claim 10 wherein the lower portion is a shank portion and the upper portion is a thigh portion.

12. An artificial joint as claimed in claim 11 wherein the latch member is positioned at the front of the knee joint.

13. An artificial joint as claimed in claim 11 wherein the latch member is positioned at the rear of the knee joint.

14. An artificial joint as claimed in claim 12 further comprising a swing phase-control means including a piston and cylinder assembly having a first end adapted to engage the upper portion and a second end adapted to engage the lower portion.

15. An artificial joint as claimed in claim 13 further comprising a swing phase-control means including a piston and cylinder assembly having a first end adapted to engage the upper portion and a second end adapted to engage the lower portion or the main body.

16. An artificial joint as claimed in claim 14 wherein the piston and cylinder assembly is hydraulic or pneumatic or a spring.

17. An artificial joint as claimed in claim 15 wherein the piston and cylinder assembly is hydraulic or pneumatic or a spring.

18. An artificial joint as claimed in claim 12 further comprising a manual locking mechanism for over-riding the automatic engagement and disengagement of the locking means.

19. An artificial joint as claimed in claim 13 further comprising a manual locking mechanism for over-riding the automatic engagement and disengagement of the locking means.

20. An artificial joint as claimed in claim 9 wherein the artificial joint is an elbow joint.

21. An artificial joint as claimed in claim 1, wherein the engaging means engages the locking means without the first body member being fully extended with respect to the second body member.

22. An artificial joint as claimed in claim 1, wherein the locking means is positioned in the front of the artificial joint.

23. An artificial joint as claimed in claim 1, wherein the locking means is positioned in the back of the artificial joint.

24. An artificial joint for providing pivotal movement between a first body member and a second body member comprising:
   (a) a main body;
   (b) a lower portion that connects to the first body member and is adapted to pivotally engage the main body about a control axis, the lower portion including a latch integral therewith which pivots only about the control axis;
   (c) an upper portion that connects to the second body member and is adapted to pivotally engage the main body about a flexing axis and having an engagement surface adapted to engage and disengage the latch upon the pivoting rotation of the upper portion relative the main body;
   (d) a resilient member adapted to engage both the main body and the lower portion configured to bias the latch to engage the engagement surface;
   (e) at least one stop surface adapted to limit motion between the main body and the lower portion; and
   (f) at least one stop surface adapted to limit motion of the upper portion;
       wherein the latch is engaged when a load is imposed on the artificial joint that passes through a line posterior to the control axis, and is disengaged when the load passes through a line anterior to the control axis.

* * * * *